(12) United States Patent
Banik et al.

(10) Patent No.: US 12,708,723 B1
(45) Date of Patent: Aug. 18, 2026

(54) MULTI-PIECE CLOSURE ASSEMBLY

(71) Applicant: MEDICAL DEVICE ENGINEERING, LLC, Pompano Beach, FL (US)

(72) Inventors: Robert Banik, Hollywood, FL (US); Peter Lehel, Boca Raton, FL (US); Patrick Vitello, Pompano Beach, FL (US)

(73) Assignee: MEDICAL DEVICE ENGINEERING, LLC, Pompano Beach, FL (US)

( * ) Notice: Subject to any disclaimer, the term of this patent is extended or adjusted under 35 U.S.C. 154(b) by 677 days.

(21) Appl. No.: 18/088,004

(22) Filed: Dec. 23, 2022

Related U.S. Application Data

(60) Provisional application No. 63/293,532, filed on Dec. 23, 2021.

(51) Int. Cl.
*A61M 5/50* (2006.01)
*A61M 5/31* (2006.01)

(52) U.S. Cl.
CPC ............ *A61M 5/5086* (2013.01); *A61M 5/31* (2013.01); *A61M 2005/3101* (2013.01); *A61M 2205/60* (2013.01)

(58) Field of Classification Search
CPC .................. A61M 5/5086; A61M 5/31; A61M 2005/3101; A61M 2205/60
See application file for complete search history.

(56) References Cited

U.S. PATENT DOCUMENTS 722,943 A 3/1903 Chappell
732,662 A 6/1903 Smith
1,678,991 A 7/1928 Marschalek
1,970,631 A 8/1934 Sherman
2,186,888 A 1/1940 Tular et al.
(Continued)

FOREIGN PATENT DOCUMENTS

CN 110589435 12/2019
DE 202008018507 2/2015
(Continued)

OTHER PUBLICATIONS

Arai Tsugio, Pilfering Proof Cap, Jan. 9, 1996.

*Primary Examiner* — Theodore J Stigell
(74) *Attorney, Agent, or Firm* — Malloy & Malloy, P.L.; Jennie S. Malloy

(57) ABSTRACT

A closure assembly for a medical or other type container including one or more closures each including a housing having a hollow interior and a communicating access opening. A tip cap is removably disposed within the hollow interior of each of the one or more closures, in an accessible disposition by the medical container, via access opening. A flag structure is connected to each of the one or more housings and extends at least partially outwardly from the respective closure. A tamper evident structure is disposed on each housing of the one or more closures adjacent to the access opening and in removable restricting relation to respective ones of the tip cap, from said hollow interior, via said access opening. Each of the one or more closures may also include one or more RFID tags, having predetermined tracking capabilities, disposed on the flag structure and/or tamper evident structure.

19 Claims, 6 Drawing Sheets

(56) References Cited

U.S. PATENT DOCUMENTS 2,277,936 A 3/1942 Rosenblatt
2,459,304 A 1/1949 Blank
2,477,598 A 8/1949 Hain
2,734,665 A 2/1956 Flamm
2,739,590 A 3/1956 Yochem
2,811,283 A 10/1957 Bowen
2,823,674 A 2/1958 Yochem
2,834,346 A 5/1958 Adams
2,875,761 A 3/1959 Helmer et al.
2,888,015 A 5/1959 Hunt
2,952,255 A 9/1960 Hein, Jr.
3,122,280 A 2/1964 Goda
3,180,532 A 4/1965 Michel
3,245,567 A 4/1966 Knight
3,301,256 A 1/1967 Cowley
3,323,798 A 6/1967 Miller
3,364,890 A 1/1968 Andersen
3,368,673 A 2/1968 Johnson
3,489,268 A 1/1970 Meierhoefer
3,568,673 A 3/1971 Cowley
3,574,306 A 4/1971 Alden
3,598,120 A 8/1971 Mass
3,610,241 A 10/1971 LeMarie
3,674,181 A 7/1972 Marks et al.
3,700,215 A 10/1972 Hardman et al.
3,706,307 A 12/1972 Hasson
3,710,922 A 1/1973 Lanphere et al.
3,712,749 A 1/1973 Roberts
3,726,445 A 4/1973 Ostrowsky et al.
3,730,325 A 5/1973 Goodwin
3,747,751 A 7/1973 Miller et al.
3,850,329 A 11/1974 Robinson
3,872,867 A 3/1975 Killinger
3,904,033 A 9/1975 Haerr
3,905,375 A 9/1975 Toyama
3,937,211 A 2/1976 Merten
3,987,930 A 10/1976 Fuson
4,005,739 A 2/1977 Winchell
4,027,669 A 6/1977 Johnston et al.
4,043,334 A 8/1977 Brown et al.
4,046,145 A 9/1977 Choksi et al.
4,068,696 A 1/1978 Winchell
4,085,845 A 4/1978 Perfect
4,106,621 A 8/1978 Sorenson
4,216,585 A 8/1980 Hatter
4,216,872 A 8/1980 Bean
4,220,151 A 9/1980 Whitney
4,244,366 A 1/1981 Raines
4,252,122 A 2/1981 Halvorsen
4,271,972 A 6/1981 Thor
4,286,591 A 9/1981 Raines
4,286,640 A 9/1981 Knox et al.
4,313,539 A 2/1982 Raines
4,369,781 A 1/1983 Gilson et al.
4,420,085 A 12/1983 Wilson et al.
4,430,077 A 2/1984 Mittleman et al.
4,433,790 A 2/1984 Gibson
4,457,445 A 7/1984 Hanks et al.
4,482,071 A 11/1984 Ishiwatari
D277,783 S 2/1985 Beck
4,520,942 A 6/1985 Dwinell
4,521,237 A 6/1985 Logothetis
4,530,437 A 7/1985 Gray et al.
4,530,697 A 7/1985 Kuhlemann et al.
4,558,554 A 12/1985 Herbert
4,571,242 A 2/1986 Klien et al.
4,589,171 A 5/1986 McGill
4,608,646 A 8/1986 Goodrich et al.
4,664,259 A 5/1987 Landis
4,667,837 A 5/1987 Vitello et al.
4,676,530 A 6/1987 Nordgren et al.
4,693,707 A 9/1987 Dye
4,726,483 A 2/1988 Drozd
4,735,617 A 4/1988 Nelson et al.
4,742,910 A 5/1988 Staebler
4,743,229 A 5/1988 Chu
4,743,231 A 5/1988 Kay et al.
4,744,455 A 5/1988 Dragotta et al.
4,753,345 A 6/1988 Goodsir et al.
4,760,847 A 8/1988 Vaillancourt
4,784,493 A 11/1988 Turcheck, Jr. et al.
4,813,564 A 3/1989 Cooper et al.
4,819,784 A 4/1989 Sticht
4,832,695 A 5/1989 Rosenberg et al.
4,834,706 A 5/1989 Beck et al.
4,842,592 A 6/1989 Caggiani et al.
4,844,906 A 7/1989 Hermelin et al.
4,863,451 A 9/1989 Marder
4,906,231 A 3/1990 Young
4,919,285 A 4/1990 Roof et al.
4,936,445 A 6/1990 Grabenkort
5,007,535 A 4/1991 Meseke et al.
5,009,323 A 4/1991 Montgomery et al.
5,024,323 A 6/1991 Bolton
5,049,129 A 9/1991 Zdeb et al.
5,057,093 A 10/1991 Clegg et al.
D323,392 S 1/1992 Bryne
5,078,696 A 1/1992 Nedbaluk
5,085,332 A 2/1992 Gettig et al.
5,090,564 A 2/1992 Chimienti
5,119,975 A 6/1992 Jemielita
5,133,454 A 7/1992 Hammer
5,135,496 A 8/1992 Vetter et al.
5,148,652 A 9/1992 Herzog
5,163,922 A 11/1992 McElveen, Jr. et al.
5,165,560 A 11/1992 Ennis, III et al.
5,230,429 A 7/1993 Etheredge, III
5,236,077 A 8/1993 Hoppmann et al.
5,267,983 A 12/1993 Oilschlager et al.
5,292,308 A 3/1994 Ryan
5,293,993 A 3/1994 Yates, Jr. et al.
5,295,599 A 3/1994 Smith
5,312,367 A 5/1994 Nathan
5,312,368 A 5/1994 Haynes
5,316,163 A 5/1994 von Schuckmann
5,328,466 A 7/1994 Denmark
5,328,474 A 7/1994 Raines
5,332,113 A 7/1994 Kusler, III et al.
5,356,380 A 10/1994 Hoekwater et al.
5,370,226 A 12/1994 Gollobin et al.
5,380,295 A 1/1995 Vacca
5,402,887 A 4/1995 Shillington
5,405,339 A 4/1995 Kohnen et al.
5,456,668 A 10/1995 Ogle, II
5,458,580 A 10/1995 Hajishoreh
5,468,224 A 11/1995 Souryal
5,474,178 A 12/1995 DiViesti et al.
5,484,413 A 1/1996 Gevorgian
5,505,705 A 4/1996 Galpin et al.
5,531,695 A 7/1996 Swisher
5,540,324 A 7/1996 Knapp
5,540,666 A 7/1996 Barta et al.
5,549,571 A 8/1996 Sak
5,558,648 A 9/1996 Shields
5,584,817 A 12/1996 van den Haak
5,588,239 A 12/1996 Anderson
5,611,445 A 3/1997 Kano et al.
5,617,954 A 4/1997 Kato et al.
5,624,402 A 4/1997 Imbert
5,662,233 A 9/1997 Reid
5,674,209 A 10/1997 Yarger
5,695,470 A 12/1997 Roussigne et al.
5,699,913 A 12/1997 Richardson
5,700,247 A 12/1997 Grimard et al.
5,702,374 A 12/1997 Johnson
5,706,985 A 1/1998 Feer
5,711,443 A 1/1998 Bennett
5,713,485 A 2/1998 Liff et al.
5,776,124 A 7/1998 Wald
5,785,691 A 7/1998 Vetter et al.
5,797,885 A 8/1998 Rubin
5,807,343 A 9/1998 Tucker et al.
5,829,589 A 11/1998 Nguyen et al.
D402,766 S 12/1998 Smith et al.

(56) References Cited

U.S. PATENT DOCUMENTS 5,842,567 A 12/1998 Rowe et al.
5,876,381 A 3/1999 Pond et al.
5,883,806 A 3/1999 Meador et al.
5,884,457 A 3/1999 Ortiz et al.
5,901,866 A 5/1999 Storar
5,902,269 A 5/1999 Jentzen
5,926,922 A 7/1999 Stottle
5,951,522 A 9/1999 Rosato et al.
5,951,525 A 9/1999 Thorne et al.
5,954,203 A 9/1999 Marconi
5,954,657 A 9/1999 Rados
5,957,166 A 9/1999 Safabash
5,957,314 A 9/1999 Nishida et al.
5,963,136 A 10/1999 O'Brien
5,983,596 A 11/1999 Corniani et al.
5,989,227 A 11/1999 Vetter et al.
5,993,437 A 11/1999 Raoz
6,000,548 A 12/1999 Tsals
D419,671 S 1/2000 Jansen
6,021,824 A 2/2000 Larsen et al.
6,027,482 A 2/2000 Imbert
6,068,614 A 5/2000 Kimber et al.
D430,293 S 8/2000 Jansen
6,112,951 A 9/2000 Mueller
D431,864 S 10/2000 Jansen
6,126,640 A 10/2000 Tucker et al.
6,190,364 B1 2/2001 Imbert
6,193,688 B1 2/2001 Balestracci et al.
6,196,593 B1 3/2001 Petrick et al.
6,196,998 B1 3/2001 Jansen et al.
6,216,885 B1 4/2001 Guillaume
6,235,376 B1 5/2001 Miyazaki et al.
6,279,746 B1 8/2001 Hussaini et al.
6,280,418 B1 8/2001 Reinhard et al.
6,287,671 B1 9/2001 Bright et al.
6,322,543 B1 11/2001 Singh et al.
6,325,227 B1 12/2001 Ekkert
6,338,200 B1 1/2002 Baxa et al.
6,358,241 B1 3/2002 Shapeton et al.
6,375,640 B1 4/2002 Teraoka
6,394,983 B1 5/2002 Mayoral et al.
6,439,276 B1 8/2002 Wood et al.
6,485,460 B2 11/2002 Eakins et al.
6,488,666 B1 12/2002 Geist
6,491,665 B1 12/2002 Vetter et al.
6,500,155 B2 12/2002 Sasso
6,520,935 B1 2/2003 Jansen et al.
6,540,697 B2 4/2003 Chen
6,565,529 B1 5/2003 Kimber et al.
6,581,792 B1 6/2003 Limanjaya
6,585,691 B1 7/2003 Vitello
6,592,251 B2 7/2003 Edwards et al.
6,666,852 B2 12/2003 Niedospial, Jr.
6,682,798 B1 1/2004 Kiraly
6,726,652 B2 4/2004 Eakins et al.
6,726,672 B1 4/2004 Hanly et al.
6,764,469 B2 7/2004 Broselow
6,796,586 B2 9/2004 Werth
6,821,268 B2 11/2004 Balestracci
D501,549 S 2/2005 McAllister et al.
6,921,383 B2 7/2005 Vitello
6,935,560 B2 8/2005 Andreasson et al.
6,942,643 B2 9/2005 Eakins et al.
6,961,638 B2 11/2005 Ouellette
6,991,126 B2 1/2006 Jackel
7,036,661 B2 5/2006 Anthony et al.
7,055,273 B2 6/2006 Roshkoff
7,100,771 B2 9/2006 Massengale et al.
7,125,397 B2 10/2006 Woehr et al.
7,141,286 B1 11/2006 Kessler et al.
7,175,081 B2 2/2007 Andreasson et al.
7,182,256 B2 2/2007 Andreasson et al.
7,232,066 B2 6/2007 Anderasson et al.
7,240,926 B2 7/2007 Dalle et al.
7,258,222 B2 8/2007 Sala et al.
7,299,981 B2 11/2007 Hickle et al.
7,367,964 B2 5/2008 Heinz et al.
7,374,555 B2 5/2008 Heinz et al.
7,404,500 B2 7/2008 Marteau et al.
7,410,803 B2 8/2008 Nollert et al.
7,425,208 B1 9/2008 Vitello
7,437,972 B2 10/2008 Yeager
7,438,704 B1 10/2008 Kawashima et al.
D581,046 S 11/2008 Sudo
D581,047 S 11/2008 Koshidaka
D581,049 S 11/2008 Sudo
7,482,166 B2 1/2009 Nollert et al.
D589,612 S 3/2009 Sudo
7,497,330 B2 3/2009 Anthony et al.
7,503,453 B2 3/2009 Cronin et al.
7,588,563 B2 9/2009 Guala
7,594,681 B2 9/2009 DeCarlo
7,608,057 B2 10/2009 Woehr et al.
7,611,487 B2 11/2009 Woehr et al.
7,632,244 B2 12/2009 Buehler et al.
D608,900 S 1/2010 Giraud et al.
7,641,636 B2 1/2010 Moesli et al.
D612,939 S 3/2010 Boone, III et al.
7,681,606 B2 3/2010 Khan et al.
7,698,180 B2 4/2010 Fago et al.
7,708,035 B2 5/2010 Windmiller
7,735,664 B1 6/2010 Peters et al.
7,748,892 B2 7/2010 McCoy
7,762,988 B1 7/2010 Vitello
7,766,919 B2 8/2010 Delmotte
7,802,313 B2 9/2010 Czajka
7,886,908 B2 2/2011 Farrar et al.
7,918,830 B2 4/2011 Langan et al.
7,922,213 B2 4/2011 Werth
7,988,004 B1 8/2011 Marret et al.
8,034,041 B2 10/2011 Domkowski et al.
8,079,518 B2 12/2011 Turner et al.
8,091,727 B2 1/2012 Domkowwski
8,118,788 B2 2/2012 Frezza
8,120,484 B2 2/2012 Chisholm
8,128,605 B2 3/2012 Masi et al.
8,137,324 B2 3/2012 Bobst
8,140,349 B2 3/2012 Hanson et al.
8,151,970 B2 4/2012 McDonald et al.
8,231,585 B2 7/2012 Heinz et al.
8,252,247 B2 8/2012 Ferlic
8,257,286 B2 9/2012 Meyer et al.
8,328,082 B1 12/2012 Bochenko et al.
8,348,895 B1 1/2013 Vitello
8,353,869 B2 1/2013 Ranalletta et al.
8,413,410 B2 4/2013 Ulm et al.
8,413,811 B1 4/2013 Arendt
8,443,999 B1 5/2013 Reinders
D684,057 S 6/2013 Kwon
8,512,277 B2 8/2013 Del Vecchio
8,528,757 B2 9/2013 Bisio
8,556,074 B2 10/2013 Turner et al.
8,579,116 B2 11/2013 Pether et al.
8,591,462 B1 11/2013 Vitello
8,597,255 B2 12/2013 Emmott et al.
8,597,271 B2 12/2013 Langan et al.
8,616,413 B2 12/2013 Koyama
D701,304 S 3/2014 Lair et al.
8,672,902 B2 3/2014 Ruan et al.
8,702,674 B2 4/2014 Bochenko
8,777,910 B2 7/2014 Bauss et al.
8,777,930 B2 7/2014 Swisher et al.
8,813,944 B2 8/2014 Tanner
8,852,561 B2 10/2014 Wagner et al.
8,864,021 B1 10/2014 Vitello
8,864,707 B1 10/2014 Vitello
8,864,708 B1 10/2014 Vitello
8,911,424 B2 12/2014 Weadock et al.
8,945,082 B2 2/2015 Geiger et al.
8,978,909 B2 3/2015 Kakutani et al.
8,985,305 B2 3/2015 Wong et al.
9,016,473 B2 4/2015 Tamarindo
9,027,769 B2 5/2015 Willows et al.
9,082,157 B2 7/2015 Gibson

(56) References Cited

U.S. PATENT DOCUMENTS 9,095,667 B2 8/2015 Von Schuckman
9,101,534 B2 8/2015 Bochenko
D738,495 S 9/2015 Strong et al.
9,125,976 B2 9/2015 Uber, III et al.
D743,019 S 11/2015 Schultz
9,192,443 B2 11/2015 Tennican
9,199,042 B2 12/2015 Farrar et al.
9,199,749 B1 12/2015 Vitello et al.
9,220,486 B2 12/2015 Schweiss et al.
9,220,577 B2 12/2015 Jessop et al.
9,227,019 B2 1/2016 Swift et al.
D750,228 S 2/2016 Strong et al.
9,272,099 B2 3/2016 Limaye et al.
9,311,592 B1 4/2016 Vitello et al.
D756,777 S 5/2016 Berge et al.
9,336,669 B2 5/2016 Bowden et al.
D759,486 S 6/2016 Ingram et al.
D760,384 S 6/2016 Niunoya et al.
D760,902 S 7/2016 Persson
9,402,967 B1 8/2016 Vitello
9,427,715 B2 8/2016 Palazzolo et al.
9,433,768 B2 9/2016 Tekeste et al.
9,463,310 B1 10/2016 Vitello
D773,043 S 11/2016 Ingram et al.
9,480,801 B2 11/2016 Schiller et al.
D777,903 S 1/2017 Schultz
9,662,456 B2 5/2017 Woehr
D789,529 S 6/2017 Davis et al.
9,687,249 B2 6/2017 Hanlon et al.
9,694,948 B1 7/2017 Pakhomov et al.
9,744,304 B2 8/2017 Swift et al.
D797,928 S 9/2017 Davis et al.
D797,929 S 9/2017 Davis et al.
9,764,098 B2 9/2017 Hund et al.
9,821,152 B1 11/2017 Vitello et al.
D806,241 S 12/2017 Swinney et al.
D807,503 S 1/2018 Davis et al.
9,855,191 B1 1/2018 Vitello et al.
D815,945 S 4/2018 Fischer
9,987,438 B2 6/2018 Stillson
D825,746 S 8/2018 Davis et al.
10,039,913 B2 8/2018 Yeh et al.
D831,201 S 10/2018 Holtz et al.
D834,187 S 11/2018 Ryan
10,124,122 B2 11/2018 Zenker
10,166,343 B1 1/2019 Hunt et al.
10,166,347 B1 1/2019 Vitello
10,183,129 B1 1/2019 Vitello
10,207,099 B1 2/2019 Vitello
10,207,835 B2 2/2019 Wilhelm et al.
D842,464 S 3/2019 Davis et al.
D847,373 S 4/2019 Hurwit et al.
10,293,987 B2 5/2019 Sattig et al.
10,300,263 B1 5/2019 Hunt
10,307,548 B1 6/2019 Hunt et al.
10,315,024 B1 6/2019 Vitello et al.
10,315,808 B2 6/2019 Taylor et al.
10,376,655 B2 8/2019 Pupke et al.
D859,125 S 9/2019 Weagle et al.
10,478,262 B2 11/2019 Niese et al.
10,555,872 B1 2/2020 Thorne
10,618,711 B2 4/2020 Weir
10,695,490 B2 6/2020 Perazzo et al.
10,758,684 B1 9/2020 Vitello et al.
10,759,611 B1 9/2020 Kalm
10,773,067 B2 9/2020 Davis et al.
10,800,556 B2 10/2020 Thorne et al.
D903,865 S 12/2020 Banik et al.
10,888,672 B1 1/2021 Vitello
10,898,659 B1 1/2021 Vitello et al.
10,912,898 B1 2/2021 Vitello et al.
10,933,202 B1 3/2021 Banik
10,940,087 B2 3/2021 Thorne et al.
10,953,162 B1 3/2021 Hunt et al.
11,040,149 B1 6/2021 Banik
11,040,154 B1 6/2021 Vitello et al.
11,065,181 B2 7/2021 Davis et al.
11,097,071 B1 8/2021 Hunt et al.
11,168,818 B2 11/2021 Fangrow
11,254,514 B2 2/2022 Vienot et al.
11,278,681 B1 3/2022 Banik et al.
D948,713 S 4/2022 Banik
11,357,588 B1 6/2022 Vitello et al.
11,413,406 B1 8/2022 Vitello et al.
11,426,328 B1 8/2022 Ollmann et al.
11,471,610 B1 10/2022 Banik et al.
11,523,970 B1 12/2022 Vitello et al.
11,541,180 B1 1/2023 Vitello et al.
11,690,994 B1 7/2023 Banik et al.
11,697,527 B1 7/2023 Hendren et al.
11,779,520 B1 10/2023 Vitello
11,793,987 B1 10/2023 Vitello et al.
11,850,210 B2 12/2023 Dadachanji et al.
11,857,751 B1 1/2024 Vitello
11,872,187 B1 1/2024 Vitello et al.
11,904,149 B1 2/2024 Vitello et al.
11,911,339 B1 2/2024 Lehel et al.
12,070,591 B1 8/2024 Vitello
12,172,803 B1 12/2024 Vitello et al.
12,195,241 B1 1/2025 Vitello et al.
12,201,230 B2 1/2025 Bell
12,383,463 B1 8/2025 Vitello et al.
12,478,449 B1 11/2025 Vitello et al.
12,545,483 B1 2/2026 Vitello et al.
2001/0003150 A1 6/2001 Imbert
2001/0034506 A1 10/2001 Hirschman et al.
2001/0041866 A1 11/2001 Capes et al.
2001/0056258 A1 12/2001 Evans
2002/0007147 A1 1/2002 Capes et al.
2002/0023409 A1 2/2002 Py
2002/0046962 A1 4/2002 Vallans et al.
2002/0079281 A1 6/2002 Hierzer et al.
2002/0097396 A1 7/2002 Schafer
2002/0099334 A1 7/2002 Hanson et al.
2002/0101656 A1 8/2002 Blumenthal et al.
2002/0104770 A1 8/2002 Shapeton et al.
2002/0133119 A1 9/2002 Eakins et al.
2002/0188259 A1* 12/2002 Hickle .................. B65D 23/14
604/189
2003/0041560 A1 3/2003 Kemnitz
2003/0055685 A1 3/2003 Cobb et al.
2003/0146617 A1 8/2003 Franko, Sr.
2003/0183547 A1 10/2003 Heyman
2003/0187403 A1 10/2003 Balestracci
2004/0008123 A1 1/2004 Carrender et al.
2004/0011623 A1 1/2004 Sala
2004/0064095 A1 4/2004 Vitello
2004/0116858 A1 6/2004 Heinz et al.
2004/0129738 A1 7/2004 Stukas
2004/0173563 A1 9/2004 Kim et al.
2004/0186437 A1 9/2004 Frenette et al.
2004/0225258 A1 11/2004 Balestracci
2005/0146081 A1 7/2005 MacLean et al.
2005/0148941 A1 7/2005 Farrar et al.
2005/0209555 A1 9/2005 Middleton et al.
2006/0049948 A1 3/2006 Chen et al.
2006/0084925 A1 4/2006 Ramsahoye
2006/0089601 A1 4/2006 Dionigi
2006/0169611 A1 8/2006 Prindle
2006/0173415 A1 8/2006 Cummins
2006/0189933 A1 8/2006 Alheidt et al.
2007/0060898 A1 3/2007 Shaughnessy et al.
2007/0106234 A1 5/2007 Klein
2007/0142786 A1 6/2007 Lampropoulos et al.
2007/0191690 A1 8/2007 Hasse et al.
2007/0219503 A1 9/2007 Loop et al.
2007/0257111 A1 11/2007 Ortenzi
2008/0068178 A1 3/2008 Meyer
2008/0078146 A1 4/2008 Cirio
2008/0097310 A1 4/2008 Buehler et al.
2008/0106388 A1 5/2008 Knight
2008/0140020 A1 6/2008 Shirley
2008/0243088 A1 10/2008 Evans
2008/0302711 A1 12/2008 Windmiller

(56) References Cited

U.S. PATENT DOCUMENTS

2008/0303267 A1 12/2008 Schnell et al.
2008/0306443 A1 12/2008 Neer
2009/0008356 A1 1/2009 Gadzic et al.
2009/0062744 A1 3/2009 Weilbacher et al.
2009/0084804 A1 4/2009 Caspary et al.
2009/0099552 A1 4/2009 Levy et al.
2009/0149815 A1 6/2009 Kiel et al.
2009/0166311 A1 7/2009 Claessens
2009/0212954 A1 8/2009 Adstedt et al.
2009/0326481 A1 12/2009 Swisher et al.
2010/0050351 A1 3/2010 Colantonio et al.
2010/0051491 A1 3/2010 Lampropoulos et al.
2010/0084403 A1 4/2010 Popish et al.
2010/0089862 A1 4/2010 Schmitt
2010/0126894 A1 5/2010 Koukol et al.
2010/0179822 A1 7/2010 Reppas
2010/0211016 A1 8/2010 Palmer-Felgate
2010/0228226 A1 9/2010 Nielsen
2010/0252564 A1 10/2010 Martinez et al.
2010/0283238 A1 11/2010 Deighan et al.
2010/0307108 A1 12/2010 Sink et al.
2011/0009836 A1 1/2011 Chebli et al.
2011/0044850 A1 2/2011 Solomon et al.
2011/0046550 A1 2/2011 Schiller et al.
2011/0046603 A1 2/2011 Felsovalyi et al.
2012/0064515 A2 3/2012 Knapp et al.
2012/0096957 A1 4/2012 Ochman
2012/0110950 A1 5/2012 Schraudolph
2013/0018356 A1 1/2013 Prince et al.
2013/0018536 A1 1/2013 Prince et al.
2013/0037383 A1 2/2013 Iwasa et al.
2013/0056130 A1 3/2013 Alpert et al.
2013/0088354 A1 4/2013 Thomas
2013/0145725 A1 6/2013 Bianco et al.
2013/0237949 A1 9/2013 Miller
2013/0269592 A1 10/2013 Heacock et al.
2014/0000781 A1 1/2014 Franko, Jr.
2014/0034536 A1 2/2014 Reinhardt et al.
2014/0069202 A1 3/2014 Fisk
2014/0069829 A1 3/2014 Evans
2014/0076840 A1 3/2014 Graux et al.
2014/0135738 A1 5/2014 Panian
2014/0155868 A1 6/2014 Nelson et al.
2014/0163465 A1 6/2014 Bartlett, II et al.
2014/0257843 A1 9/2014 Adler et al.
2014/0319141 A1 10/2014 Stratis et al.
2014/0326727 A1 11/2014 Jouin et al.
2014/0353196 A1 12/2014 Key
2014/0358078 A1 12/2014 Fischer et al.
2015/0013811 A1 1/2015 Carrel et al.
2015/0048045 A1 2/2015 Miceli et al.
2015/0112296 A1 4/2015 Ishiwata et al.
2015/0136632 A1 5/2015 Moir et al.
2015/0182686 A1 7/2015 Okihara
2015/0191633 A1 7/2015 De Boer et al.
2015/0246185 A1 9/2015 Heinz
2015/0251820 A1 9/2015 Glaser et al.
2015/0298414 A1 10/2015 Dittmer et al.
2015/0302232 A1 10/2015 Strassburger et al.
2015/0305982 A1 10/2015 Bochenko
2015/0310771 A1 10/2015 Atkinson et al.
2016/0067144 A1 3/2016 Chang
2016/0067422 A1 3/2016 Davis et al.
2016/0090456 A1 3/2016 Ishimaru et al.
2016/0136352 A1 5/2016 Smith et al.
2016/0144119 A1 5/2016 Limaye et al.
2016/0158110 A1 6/2016 Swisher et al.
2016/0158449 A1 6/2016 Limaye et al.
2016/0176550 A1 6/2016 Viitello et al.
2016/0194121 A1 7/2016 Ogawa et al.
2016/0250420 A1 9/2016 Maritan et al.
2016/0279032 A1 9/2016 Davis
2016/0328586 A1 11/2016 Bowden et al.
2016/0361235 A1 12/2016 Swisher
2016/0367439 A1 12/2016 Davis et al.
2017/0007771 A1 1/2017 Duinat et al.
2017/0014310 A1 1/2017 Hyun et al.
2017/0124289 A1 5/2017 Hasan et al.
2017/0173321 A1 6/2017 Davis et al.
2017/0203086 A1 7/2017 Davis
2017/0225843 A1 8/2017 Glaser et al.
2017/0239141 A1 8/2017 Davis et al.
2017/0297781 A1 10/2017 Kawamura
2017/0319438 A1 11/2017 Davis et al.
2017/0328758 A1 11/2017 Fuchs
2017/0349335 A1 12/2017 Sattig et al.
2017/0354792 A1 12/2017 Ward
2018/0001540 A1 1/2018 Byun
2018/0014998 A1 1/2018 Yuki et al.
2018/0064604 A1 3/2018 Drmanovic
2018/0078684 A1 3/2018 Peng et al.
2018/0089593 A1 3/2018 Patel et al.
2018/0098915 A1 4/2018 Rajagopal et al.
2018/0147115 A1 5/2018 Nishioka et al.
2018/0236177 A1 8/2018 Schraga
2018/0312305 A1 11/2018 Rognard
2019/0275313 A1 9/2019 Godin et al.
2019/0308006 A1 10/2019 Erekovcanski et al.
2019/0388626 A1 12/2019 Okihara
2021/0228445 A1 7/2021 Bouteloup et al.
2021/0244892 A1 8/2021 Maritan et al.
2022/0008645 A1 1/2022 Ukai et al.
2022/0024630 A1 1/2022 Bohamed
2022/0257467 A1 8/2022 Yano et al.
2022/0296470 A1 9/2022 Wagner
2022/0339067 A1 10/2022 Christine et al.
2023/0036805 A1 2/2023 Rey

FOREIGN PATENT DOCUMENTS

DE 102020123373 3/2020
DE 102020123392 3/2022
DE 102020131870 6/2022
EP 0148116 7/1985
EP 269920 6/1988
EP 571980 12/1993
EP 2724977 4/2014
EP 2937616 10/2015
GB 486367 6/1938
GB 2102774 2/1983
JP 08002544 1/1996
JP 2014076618 5/2014
KR 101159987 6/2012
KR 101868822 6/2018
WO WO8607040 12/1986
WO WO9118801 12/1991
WO WO1992003348 3/1992
WO WO2008000279 1/2008
WO WO2017086607 5/2015
WO WO2025003684 1/2025

* cited by examiner

MULTI-PIECE CLOSURE ASSEMBLY

CLAIM OF PRIORITY

The present application claims priority under 35 U.S.C. Section 119 to a U.S. Provisional application having Ser. No. 63/293,532 and filed on Dec. 23, 2021, which is incorporated by reference herein in its entirety.

BACKGROUND OF THE INVENTION

Field of the Invention

The present invention is directed to a multi-piece closure assembly, including at least one but more practically, a plurality of closures for a container specifically including, but not limited to, a medical container such as a syringe. The one or more closures may include structure enabling radiofrequency identification (RFID) capabilities for tracking initial use and/or administration of the contents of the container.

Description of the Related Art

In the medical field, it is a relatively common for authorized medical personnel to prescribe a drug or medication for a patient which is to be given by injection or other procedures, such as administering fluids to the patient by intravenous (IV) infusion. It is also relatively common procedure for syringes and other drug administering devices to be pre-loaded or filled by pharmacists or other authorized personnel, whether within the hospital or at another facility and location. However, such locations are typically located in a remote part of the hospital or other facility, relative to the patient care area where the injection is to be administered. Indeed, large medical facilities may include a location on the hospital grounds where drugs and other fluids are delivered to multiple nursing stations at different locations. Because of the remote location of many nurse's stations relative to a filling location, a fluid or drug loaded administering device is very often given to another person for delivery to a nurse's station for subsequent dosing of the patient by a duly qualified nurse or other medically trained person. As a result, a pre-loaded syringe May travel quite some distance and be handled by several people before it reaches a nurse's station, which raises some concern that the contents of the syringe may be tampered with or cause the sterility of the syringe and/or its contents to be compromised.

Additionally, in the case where a drug has been prescribed that is very expensive or addictive such as, but not limited to, morphine, has been pre-loaded in the syringe or other administering device, there is a danger that the pre-loaded syringe or other administering device will be tampered with at some point, by a person seeking unauthorized access to the drug. This possibility can present a real danger if such a person were to gain access to the prescribed medicine and then, inappropriately and without concern, substitute some other, unauthorized material in the syringe which looks like the actual prescribed medicine and dosage. By way of example only, if saline solution or water or another drug were substituted for a dose of morphine, the patient would not receive the prescribed drug which by itself, could be quite harmful, while the substituted content might potentially also cause serious harm. Thus, there is a problem of knowing if a sealed, pre-loaded syringe or other administering device has, or has not, been exposed to contamination or might otherwise have been compromised by its being tampered with.

More specifically, and in order to overcome the disadvantages and concerns associated with the growing use of syringes and/or other medical containers or devices that are pre-filled with various prescribed medicines, a variety of "tamper evident structures" have been developed. Such tamper evident assemblies are structured to prevent or at least restrict access to the contents of a pre-filled syringe. If in fact, access has been accomplished or even attempted to a pre-filled syringe or other drug administering device, such tamper evident assemblies are intended to provide a clear indication of it having been tampered with.

In the field relating to closures for medical devices, it is well known that packaging, dispensing, installation, etc. of such tamper evident closures are preferably done in a relatively sterile environment. Therefore, during such processing of medical closures, it is important to maintain a degree of sterility. This is due at least in part to the fact that such tamper evident closures may be attached in closing/sealing relation to a pre-filled syringe or other type medical container having medicine or other fluids retained therein. Because the retained medicines and/or fluids are typically intended to be administered to a patient, sterility of the closure will likely be an important factor.

Moreover, conventional and prior art closures for a variety of different medical containers including, but not limited to pre-filled syringes, IV sets, infusion pump cartridge preparations of the type used in various oral, enteral and other pharmacy drug applications, are structured to demonstrate tamper evident capabilities. Frequently, structures associated with such known closures incorporate a ring or other indicator member removably attached within the interior of a housing by one or more breakable, frangible tabs or like structures.

Accordingly, use or attempted access to a contained tip cap during dispensing involves removal of the exterior housing, which in turn, results in a breakage or separation of the indicator ring or like structure from the housing, along with the tip cap. Access to the contained medication or fluid within the syringe or other medical container involves a removal of the tip cap and frequently, removal of the indicator ring or like indicator structure. However, once the indicator ring is broken or separated from the interior of the housing, small parts of the frangible tabs or like breakable connecting structure may become exposed to the user, and possibly a patient, during administration and/or removal of the indicator ring from the syringe or other medical container.

Additional disadvantages associated with such known frangible indicators is the design structuring and manufacture of the indicator member and connecting frangible structure in a manner which will survive shipping, handling and inadvertent breakage during attempted access.

Therefore, there is a need in this field of art for a closure assembly which overcomes the problems and disadvantages, of the type set forth above, which remain in various existing medical closure structures. If any such improved closure assembly were developed, it would preferably include a tamper evident structure disposed in removal restricting, interruptive engagement with a tip cap disposed within a housing and which facilitates access to but restricted removal of the tip cap from, while preventing any full breakage or complete disconnection of components of the tamper evident structure.

SUMMARY OF THE INVENTION

The present invention is directed to a closure assembly including one or more closures for a container specifically including, but not limited to, a medical container. As a non-limiting example, when the medical container is in the form of a syringe, it may be pre-filled with any one of a plurality of different compositions intended for dispensing and/or administration in a generally known manner.

In the illustrated embodiment, the one or more closures each include a housing having a hollow interior and an access opening communicating with the hollow interior. The access opening is disposed, dimensioned and configured for passage therethrough of a connecting part of the medical container, such as a discharge port or channel of a syringe. In cooperation therewith, a tip cap is removably disposed within the hollow interior of each of the plurality of closures, in an accessible disposition for the connecting part/discharge channel of the medical container, as the medical container passes through the access opening. As practiced, the tip cap is cooperatively structured with the discharge port, discharge channel or other type connecting part of the medical container to be connected thereto in a manner which prevents or restricts fluid flow from the medical container.

Additionally, in at least one embodiment of the invention, each of the one or more closures includes a flag structure including a base, and an at least minimally elongated arm extending outwardly from the base. As such, the base of each of the one or more flag structures is connected to a different housing at least partially coincident to the access opening. In such a disposition, the base may be attached to the outer rim and/or periphery of the access opening and, in one or more embodiments, in at least partially covering relation to the access opening and in at least partially overlying relation to the corresponding hollow interior. Concurrently, the elongated arm of each of the flag structures extends outwardly from its base and accordingly, outwardly from the respective housing of the closure to which the base is attached.

In addition, another feature of the one or more embodiments of the closure assembly of the present invention includes each of the one or more closures having a tamper evident structure disposed thereon. As explained in greater detail hereinafter, each tamper evident structure may be integrated in the flag structure, including the base thereof, or otherwise connected to the base such that the base and the tamper evident structure are concurrently mounted on the housing, at least partially coincident to the access opening thereof.

Further, in at least one embodiment, the tamper evident structure includes an aperture formed therein in communicating and/or axial alignment with the access opening, when the tamper evident structure is mounted on the housing. Such communicating and/or axial alignment with the aperture of the tamper evident structure is accomplished, at least in part, by it being disposed on the housing and dimensioned and configured to extend inwardly from a periphery of the access opening and/or from a location substantially adjacent to the periphery of the access opening, inwardly toward the center of the access opening. In such a preferred disposition, the tamper evident structure and the aperture formed therein is positioned in overlying relation to the hollow interior, such that the tamper evident structure only partially closes and/or covers portions to the access opening inwardly adjacent to the periphery thereof. As a result, the tamper evident structure is disposed on said housing in removable restricting relation to the tip cap, such as when the tip cap is attempted to be removed from the hollow interior through the access opening.

The removable restricting relation of the tamper evident structure relative to the tip cap can be explained in more specific terms, by cooperative structuring which includes a diametrical dimension of the tip cap being less than a diametrical dimension of the access opening of the housing in which it is disposed. Also, the diametrical dimension of the tip cap is greater than the diametrical dimension of the aperture in the tamper evident structure. In cooperation therewith, the diameter or diametrical dimension of the aperture in the tamper evident structure is sufficiently large and/or greater than that of the discharge channel or connecting part of the medical container which passes into the hollow interior of the housing and in connection with the corresponding tip cap disposed therein.

Therefore, attempts to remove the tip cap from the hollow interior of the housing, such as when attached to the medical connector results in the larger diameter tip cap coming into removable restricting engagement with the tamper evident structure. In at least one embodiment, the tamper evident structure is formed from a foil material or other material capable of being ripped or torn when sufficient force is exerted thereon, such as when the tip cap attempts to pass through the aperture of the tamper evident structure, out of the hollow interior through the aperture. As indicated, the material, from which the tamper evident structure is formed will rip or tear, but preferably not detach from a remainder of the tamper evident structure, as the relatively larger tip cap is forced to pass through the smaller dimensioned aperture in the tamper evident structure. Such ripping, tearing or other visually evident damaging of the tamper evident structure will provide a clear indication of tampering and/or attempted use and removal of the tip cap from the hollow interior of the housing in which it is disposed.

One embodiment of the closure assembly of the present invention includes the one or more closures including radiofrequency identification (RFID) capabilities. In one embodiment, such RFID capabilities are provided in the form of an RFID tag preferably mounted on the flag structure such as, but not limited to the arm thereof. Further, one embodiment of the present invention includes the RFID tag being removably secured to the tag such as by an adhesive and/or reusable adhesive. In this embodiment, the removable RFID tag may be removed from the arm of the flag structure and secured to the syringe or other type container until the contents of the syringe or container are fully dispensed or administered. Upon such complete usage of the contents of the medical container, it may be disposed of, along with the RFID tag secured thereto. Accordingly, in this embodiment the RFID tag includes tracking capabilities which enable the tracking of the usage of the contents of the medical container and/or at least when the administration thereof has been completed.

Yet another embodiment of the present invention includes a tamper evident structure mounted on the base of a flag structure in removable restricting relation to a correspondingly disposed tip cap within the hollow interior of a common housing. In this embodiment, the housing and at least a portion of the corresponding flag structure are substantially common to other embodiments of the closure as described herein. However, the tamper evident structure, while operationally similar, is structurally modified to eliminate the aperture formed therein. In contrast, the tamper evident structure is dimensioned, disposed and configured to entirely cover and close the access opening and thereby substantially enclose the hollow interior of the housing to which it is attached. As a result, this embodiment provides the tamper evident structure at least partially defining a "sterile barrier" by enhancing the sterility of the tip cap by enclosing it within the hollow interior, without it being exposed to the exterior or surrounding exterior environment of the housing.

Moreover, as with the initial embodiment, the sterile barrier tamper evident structure is also formed of a foil or other at least partially similar material which is capable of being penetrated by a forced positioning (penetration) of the medical container and its connecting part through the sterile barrier version of the tamper evident structure causing it to rip or tear. Such ripping, tearing or other rupturing thereof will provide a clear indication of tampering or attempted use and access to the enclosed tip cap.

Yet additional features of this embodiment of the closure assembly of the present invention include an additional or secondary RFID tag secured to the enclosing tamper evident structure. This secondary RFID tag, along with the first or primary RFID tag secured to the flag structure also includes tracking capabilities. Accordingly, upon force penetration and rupture (ripping, tearing, etc.) of the enclosing tamper evident structure by forced entry of the medical container into the hollow interior, the secondary RFID tag will be destroyed and thereby deactivated. Such a deactivation will provide an indication, through tracking capabilities associated with the secondary RFID tag, of initial use of each of the one or more closures as the connecting part of the medical container passes into the hollow interior of a given housing into connecting engagement with the enclosed tip cap.

For purposes of clarity, it is to be noted that radiofrequency identification tags of the type referred to herein are operative to use electromagnetic fields to automatically identify and track components to which an RFID tag is attached. Further the operative features of an RFID system include a radio transponder, radio receiver and transmitter. When triggered by an electromagnetic interrogation pulse from an RFID reader device, the RFID tag transmits digital data such as, but not limited to an identity number. In addition, the primary and secondary RFID tags as used herein may be either passive tags powered by energy from an RFID reader or in the alternative the primary and secondary RFID tags may be active such as by being powered by a battery or other power source. As should be apparent and commonly recognized, active tags may be read/tracked at greater ranges or distances from a given RFID reader system.

The structural and operative features of the closure assembly of the present invention facilitate the organized and/or automated capping of a plurality of syringes or other medical containers. In more specific terms, a plurality of closures assembled to have the aforementioned flag structures connected thereto in an operative disposition are disposed in a "capping orientation". Such capping orientation may be defined as an elongated strip of the plurality of closures being disposed in interconnected relation to one another. Further, such interconnected relation is at least partially defined by the arm portions of the flag structures being removably attached or connected to next adjacent arms of the next adjacent closures disposed in the elongated strip. As indicated, due to the fact that the diameter of the connecting part of the syringe or other medical container is less than the diameter of the aperture formed in the tamper evident structure, the connecting part can pass into the hollow interior through the aperture and corresponding access opening into connecting engagement with the enclosed tip cap, without damage to the tamper evident structure.

Thereafter, the plurality of closures in the elongated strip can be separated by disconnecting adjacent ones of the arms of the flag structures. In turn, this results in the housing of each closure being disposed on and in surrounding relation to the connecting part of the syringe or other medical container attached to a tip cap within the hollow interior. Upon use, dispensing, administration of the contents of the syringe, the tip cap will be forced out of the hollow interior through the aperture of the tamper evident structure resulting in a tearing, ripping, etc. thereof and thereby providing a visual indication of tampering, or intended use.

Accordingly, the present invention is directed to a closure assembly including at least one but more practically a plurality of multi-part closures structured to provide a clear indication of tampering or attempted use and also including tracking capabilities due to the provision of one or more RFID tags associated with each of the one or more closures.

These and other objects, features and advantages of the present invention will become clearer when the drawings, as well as the detailed description, are taken into consideration.

BRIEF DESCRIPTION OF THE DRAWINGS

For a fuller understanding of the nature of the present invention, reference should be had to the following detailed description taken in connection with the accompanying drawings in which.

Like reference numerals refer to like parts throughout the several views of the drawings.

DETAILED DESCRIPTION OF THE PREFERRED EMBODIMENT

Figure 1:
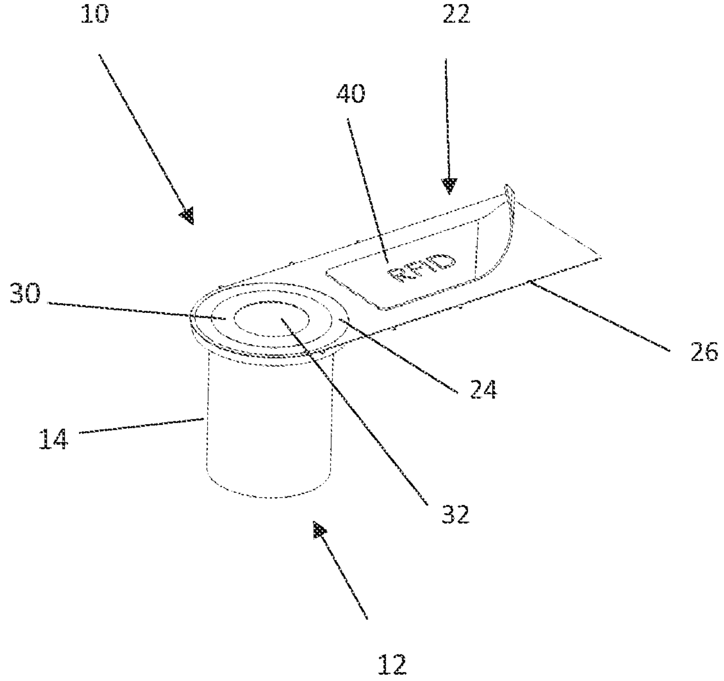
FIG. 1 is a perspective view of a single closure one embodiment of the closure assembly of the present invention.

The invention will now be described more fully hereinafter with reference to the accompanying drawings in which illustrative embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

The present invention is directed to a closure assembly generally indicated as 10 including one or more closures 12 for a container (not shown) specifically including, but not limited to, a medical container. By way of non-limiting example, when the medical container is in the form of a syringe, it may be pre-filled with any one of a plurality of different compositions intended for dispensing and/or administration in a generally known manner.

The one or more closures 12 each include a housing 14 having a hollow interior 16 and an access opening 18 communicating with the hollow interior 16. The access opening 18 is disposed, dimensioned and configured for passage therethrough of a connecting part of the medical container, such as a discharge port or channel of a syringe. In cooperation therewith, a tip cap 20 is removably disposed within the hollow interior 16 of each of the plurality of closures 12 in an accessible disposition for the connecting part/discharge channel of the medical container, as the medical container passes through the access opening 18. As practiced, the tip cap 20 is cooperatively structured with the discharge port, discharge channel or other type connecting part of the medical container to be connected thereto in a manner which prevents or restricts fluid flow from the medical container.

Each of the one or more closures 12 include a flag structure 22 including a base 24 and an at least minimally elongated arm 26 extending outwardly from the base 24. As such, the base 24 of each of the one or more flag structures 22 is connected to a different housing 14 at least partially coincident to the access opening 18. In such a disposition, the base 24 may be attached to the outer rim and/or periphery 18' of the access opening 18 (see FIG. 2). In one or more embodiments, the base 24 is disposed in direct connection to the rim or periphery 18' and extends outwardly therefrom in at least partially covering relation to the access opening 18 and in at least partially overlying relation to the hollow interior 16. Concurrently, the elongated arm 26 of each of the flag structures 22 extends outwardly from its base 24 and accordingly outwardly from the respective housing 14 of the closure 12 to which it is attached.

Another feature of the one or more embodiments of the closure assembly 10 include each of the one or more closures 12 having a tamper evident structure 30 disposed thereon. As explained in greater detail hereinafter, each tamper evident structure 30 may be integrated in the flag structure 22, including the base 24 thereof, as represented throughout the Figures, or otherwise connected to the base 24 such that the base 24 and the tamper evident structure 30 are concurrently mounted on the housing 12, at least partially coincident to the access opening 18 thereof. Moreover, as also represented throughout the Figures, the tamper evident structure 30 may include a substantially annular configuration including an aperture 32 formed in at least partially surrounded relation to the annularly configured tamper evident structure 30.

Further, in at least one embodiment the tamper evident structure 30 includes the aperture 32 disposed in communicating and/or axial alignment with the access opening 18, when the tamper evident structure 30 is mounted on the housing 14, concurrently to the base 24 of the corresponding flag structure 22. Such communicating and/or axial alignment with the aperture 32 of the tamper evident structure 30 is accomplished, at least in part, by it being disposed to extend and/or being spaced inwardly from the periphery or rim 18' of the access opening 18. Moreover, in that at least in one embodiment of the tamper evident structure 30 is connected to or integrated in the base 24 of the flag structure 22, and may extend inwardly from an area adjacent to the periphery or rim 18', to which an outer peripheral portion of the base 24 is attached. In such a preferred disposition, the tamper evident structure 30 and the aperture 32 formed therein is positioned in overlying relation to the hollow interior 16, such that the tamper evident structure 30 only partially closes and/or covers interior or substantially center portions to the access opening 18. As a result, the tamper evident structure 30 is disposed on said housing 14 in removable restricting relation to the tip cap 20, such as when the tip cap 20 is attempted to be removed from the hollow interior 16 through the aperture 32 and/or access opening 18.

This removable restricting relation of the tamper evident structure 30 relative to the tip cap 20 can be explained in more specific terms, by cooperative structuring of the components of the one or more closures 12. Such cooperative structuring includes a diameter or diametrical dimension of the tip cap 20 being less than a diameter or diametrical dimension of the access opening 18 of the housing 14 in which it is disposed. Also, the diameter or diametrical dimension of the tip cap 20 is greater than the diameter or diametrical dimension of the aperture 32. In cooperation therewith, the diameter or diametrical dimension of the aperture 32 of the tamper evident structure 30 is sufficiently large and/or greater than that of the discharge channel or connecting part of the medical container, which passes into the hollow interior 16 of the housing 14 and in connection with the corresponding tip cap 20 disposed therein.

Figure 2:
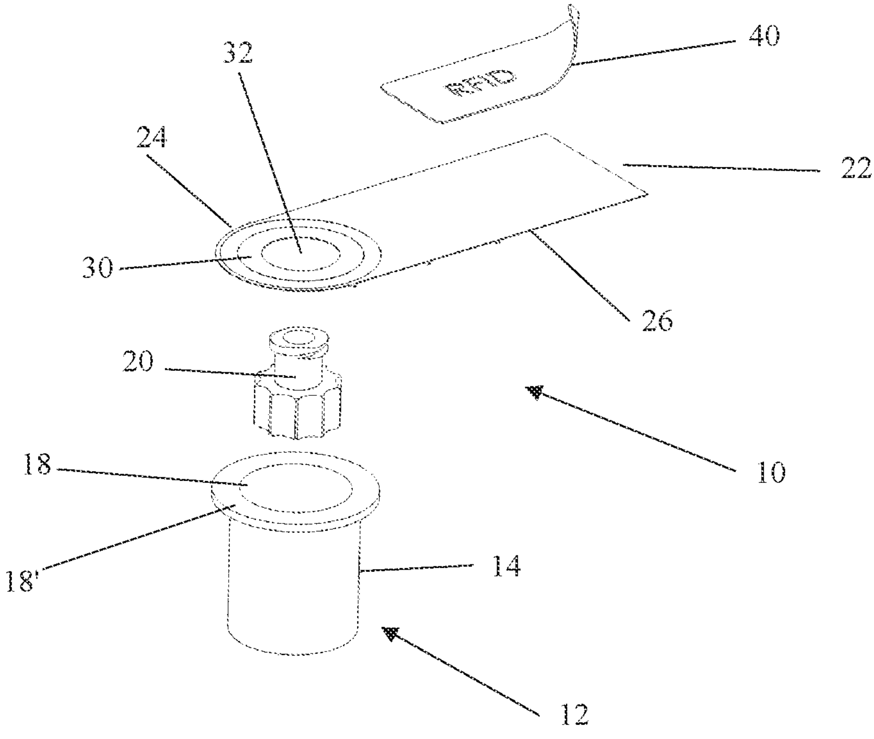
FIG. 2 is a perspective view in an exploded form of the embodiment of FIG. 1.
Figure 4:
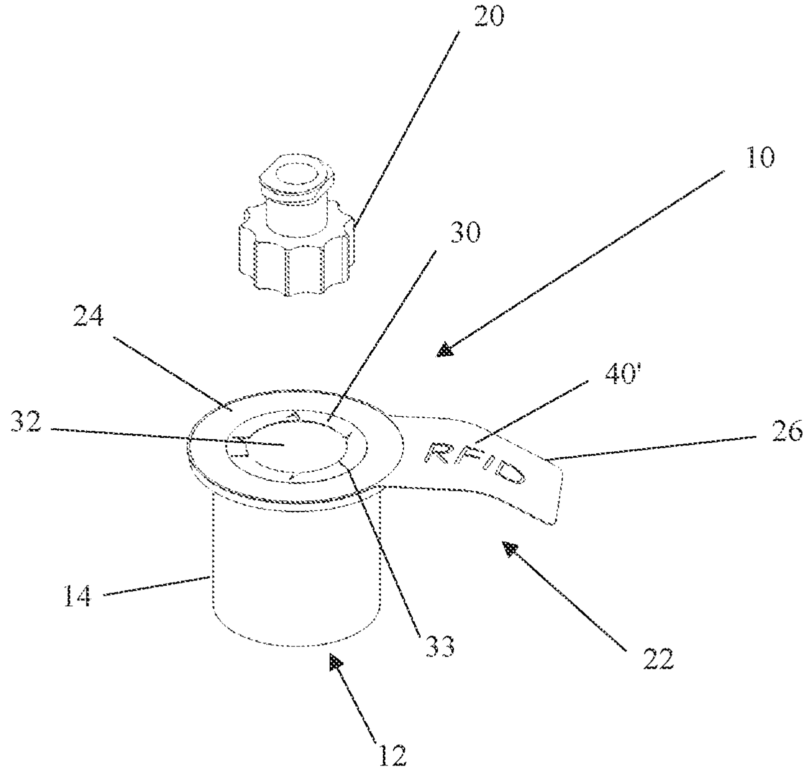
FIG. 4 is a perspective view in partially exploded form of the embodiment of FIG. 3.

Therefore, attempts to remove the tip cap 20 from the hollow interior 16, such as when attached to the medical connector, results in the larger diameter tip cap 20 coming into removable restricting, interruptive engagement with the under or inner surface portions of the tamper evident structure 20, as represented in at least FIGS. 2 and 4. In at least one embodiment, the tamper evident structure 30 is formed from a foil material or other material capable of being ripped or torn when sufficient pressure or force is exerted thereon, such as when the tip cap 20, once connected to the medical container, attempts to pass or be pulled through the aperture 32 of the tamper evident structure 30, out of the hollow interior 16. As indicated, the material, from which the tamper evident structure 30 is formed will rip or tear, as at 33, in FIG. 4. However, the foil or like material being ripped or torn, as at 33, will not become detached from a remainder of the tamper evident structure 30, as the relatively larger tip cap 20 is forced to pass through the smaller dimensioned aperture 32. Such ripping, tearing or other visually evident damaging of the tamper evident structure 30 will provide a clear indication of tampering and/or attempted use and removal of the tip cap from the hollow interior of the housing in which it is disposed.

Accordingly, one distinct advantage of forming the tamper evident structure 30 from a material such as foil, which rips, tears, etc. rather than becoming detached is the elimination of any detached particles, portions, etc. coming free from the respective closure 12 and possibly contaminating a patient or an administrative site. Such detached particles may be more commonplace with closures for medical and/or other containers which have a frangible construction facilitating the breakage of comparatively hard or rigid plastic or other frangible material structures.

One embodiment of the closure assembly of the present invention includes the one or more closures including radiofrequency identification (RFID) capabilities. In one embodiment, such RFID capabilities are provided in the form of at least one RFID tag 40 preferably mounted on the flag structure 22 such as, but not limited to the arm 26, as represented in the accompanying Figures. Also, one embodiment of the closure assembly 10 includes the RFID tag 40 being removably secured to the flag structure 22 and/or arm 26 such as by an adhesive and/or reusable adhesive, as at least schematically represented in FIGS. 1 and 2. In this embodiment, the removable RFID tag 40 may be removed from the arm 26 of the flag structure 22 and secured to the syringe or other type container until the contents of the syringe or container are fully dispensed or administered. Upon such complete usage of the contents of the medical container, the container may be disposed of, along with the RFID tag 40 secured thereto, thereby possibly causing its deactivation. Accordingly, in this embodiment the RFID tag 40 includes tracking capabilities which enable the tracking of the usage of the contents of the medical container and/or at least when the administration thereof has been completed.

Figure 3:
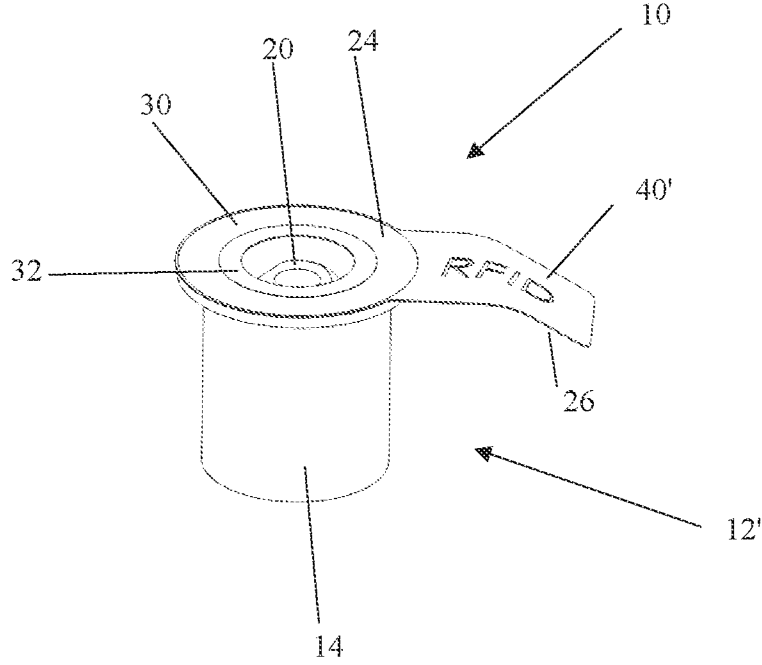
FIG. 3 is a perspective view of one other embodiment of a closure of the closure assembly of the present invention.

However, it is noted that in the embodiment of FIGS. 3 and 4 the RFID tag 40' may be integrated in or otherwise iteratively attached to the flag structure 22, specifically including the arm 26 thereof. In this embodiment, the RFID tag 40' is not removable from the flag structure 22 due to the aforementioned substantially integrated construction.

Yet another embodiment of the closure assembly 10 includes a tamper evident structure mounted on the base of a flag structure 22 in removable restricting relation to a correspondingly disposed tip cap 20 within the hollow interior 16 of a common housing 14. In this additional embodiment, the structure of the housing 14 and at least a portion of the corresponding flag structure 22 are substantially common to other embodiments of the closure 12 as described herein. However, the tamper evident structure in this additional embodiment, while operationally similar, is structurally modified to eliminate the aforementioned aperture 32 formed therein. In contrast, the tamper evident structure is dimensioned, disposed and configured to entirely cover and close the access opening 18 and thereby substantially enclose the hollow interior 16 of the housing 14 to which it is attached. As a result, this embodiment provides the tamper evident structure at least partially defining a "sterile barrier" by enhancing the sterility of the tip cap 20 by enclosing it within the hollow interior 16, thereby preventing its initial or continuous exposure to the exterior surroundings prior to the tip cap 20 being connected to the medical container.

Moreover, as with the initial embodiment as represented throughout FIGS. 1-6, the sterile barrier tamper evident structure is also formed of a foil or other at least partially similar material which is capable of being penetrated by a forced positioning (penetration) of the medical container and its connecting part through the sterile barrier version of the tamper evident structure causing it to rip or tear. Such ripping, tearing or other rupturing thereof will provide a clear indication of tampering or attempted use and access to the enclosed tip cap.

Yet additional features of this embodiment of the closure assembly of the present invention includes an additional or secondary RFID tag secured to the enclosing tamper evident structure. This secondary RFID tag, along with the first or primary RFID tag 40 or 40' secured to the flag structure 22 also includes tracking capabilities. Accordingly, upon forced penetration and rupture (ripping, tearing, etc.) of the enclosing tamper evident structure by forced entry of the medical container into the hollow interior 16, the secondary RFID tag will be destroyed and thereby deactivated. Such deactivation will provide an indication, through activation of the tracking capabilities associated with the secondary RFID tag, of initial use of each of the one or more closures 12 as the connecting part of the medical container passes into the hollow interior 16 of a given housing 14 into connecting engagement with the enclosed tip cap 20.

For purposes of clarity, it is to be noted that radiofrequency identification tags, of the type referred to herein are operative to use electromagnetic fields to automatically identify and track components to which an RFID tag is attached. Further the operative features of an RFID system include a radio transponder, radio receiver and transmitter. When triggered by an electromagnetic interrogation pulse from an RFID reader device, the RFID tag transmits digital data such as, but not limited to an identity number. In addition, the primary and secondary RFID tags as used herein may be either passive tags powered by energy from an RFID reader or in the alternative the primary and secondary RFID tags may be active such as by being powered by a battery or other power source. As should be apparent and commonly recognized active tags may be read/tracked at greater ranges or distances from a given RFID reader system.

Figure 6:
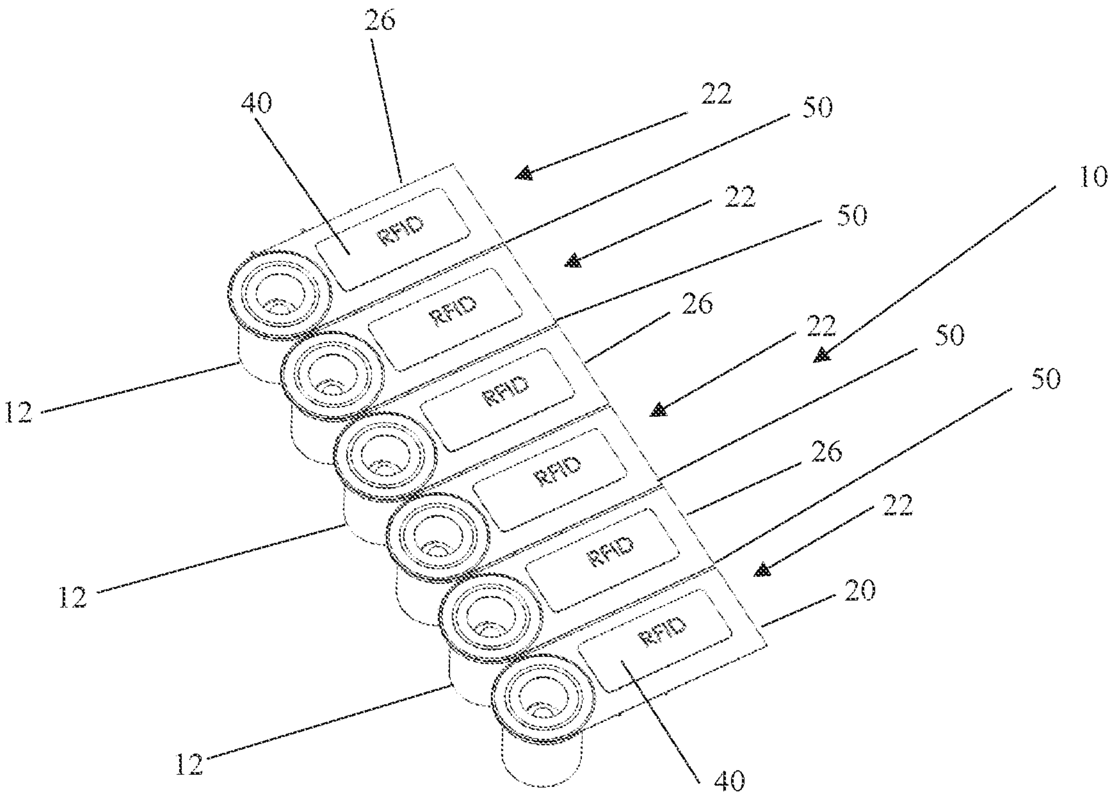
FIG. 6 is a perspective exterior view of the embodiment of FIG. 5.

As represented in FIG. 6, the structural and operative features of the closure assembly 10 facilitate the organized and/or automated capping of a plurality of syringes or other medical containers with the tip cap 20 in the hollow interior 16 of the plurality of closures 12. In more specific terms, the plurality of closures 12, which have been assembled to have the flag structures 22 connected thereto in an operative disposition are disposed in a "capping orientation". Such capping orientation may be defined as an elongated strip of the plurality of closures 12 being disposed in interconnected relation to one another. Such interconnected relation is at least partially defined by the arm portions 26 of the flag structures 22 being removably attached or connected to next adjacent arms 26 of the next adjacent closures 12, along weakened seam lines 50. As indicated in FIG. 6, the weakened seam lines extend along both, oppositely disposed longitudinal peripheral edges of the arms 26 of the flag structures 22. The weakened structure of the seam lines facilitates easy separation of the adjacent arms 26, subsequent to capping.

As indicated, the diameter of the connecting part of the syringe or other medical container is less than the diameter of the aperture 32 formed in the tamper evident structure 30, the connecting part of the medical container can therefore pass into the hollow interior 16 through the aperture 32 and corresponding access opening 18 into connecting engagement with the enclosed tip cap 20, without damaging the tamper evident structure 30.

Thereafter, the plurality of closures 12 in the elongated strip can be separated by disconnecting adjacent ones of the arms 26 of the flag structures 22. In turn, this results in the housing 14 of each closure 12 being disposed on and in surrounding relation to the connecting part of the syringe or other medical container attached to a tip cap 20 within the hollow interior 16. Upon use, dispensing, administration of the contents of the syringe the tip cap 20 will be forced out of the hollow interior 16 through the aperture 32 of the tamper evident structure 30 resulting in a tearing, ripping, etc. thereof and thereby providing a visual indication of tampering, or intended use.

Figure 5:
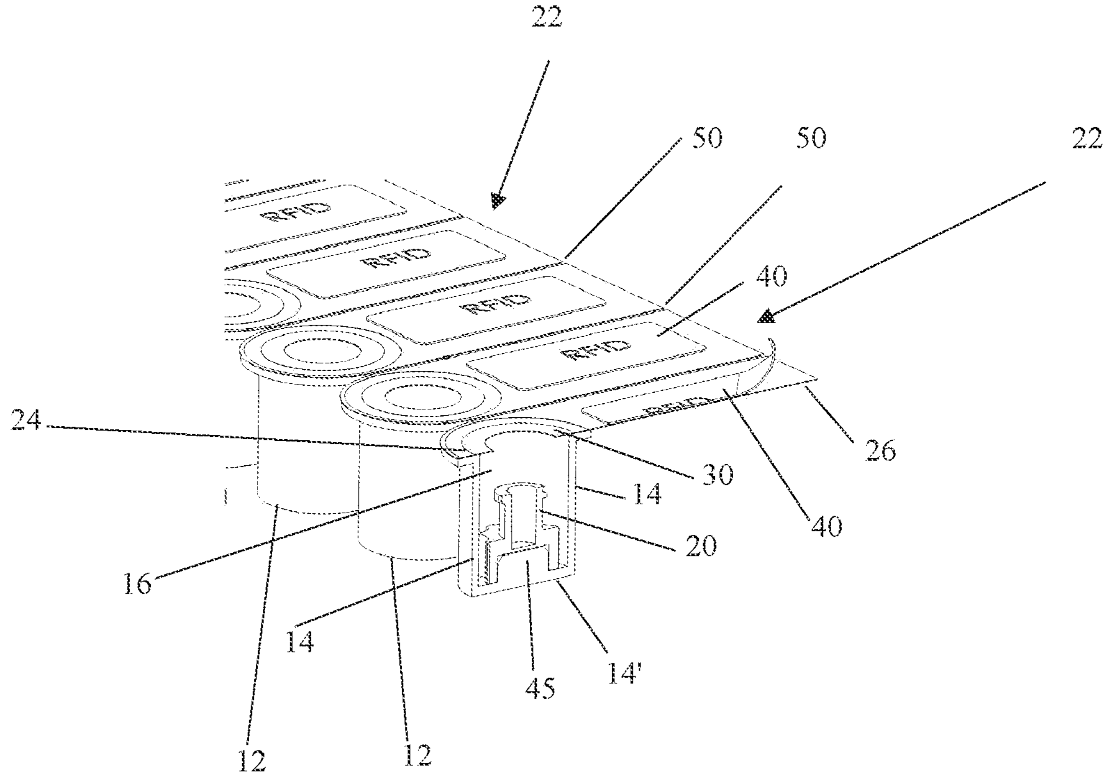
FIG. 5 is a perspective interior view in partial cutaway of yet another embodiment of the closure assembly of the present invention.

With further reference to FIG. 5 attachment between the discharge channel or other connecting part of the medical container to the tip cap 20 may be by a rotational or threaded connection. When the tip cap 20 is so structured it and the bottom or closed-end 14' of the housing 14 may include a one-way drive assembly generally indicated as 45. In turn, the one-way drive assembly 45 may comprise a "ramp and cliff" type one-way drive structure as of the type, but not limited to that represented in U.S. Pat. No. 8,591,462. However, dependent on the structural features of the tip cap 20 the connecting part of the medical container may be attached to and enclosed tip cap 20 in a different manner.

Accordingly, the present invention is directed to a closure assembly including at least one but more practically a plurality of multi-part closures structured to provide a clear indication of tampering or attempted use and also including tracking capabilities due to the provision of one or more RFID tags associated with each of the one or more closures.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

What is claimed is:

1. A closure assembly for a medical container comprising:

at least one closure including a housing, said housing having a hollow interior and an access opening communicating with said hollow interior, a tip cap removably disposed within said hollow interior in an accessible disposition, via said access opening, a flag structure connected to said housing and at least partially extending outwardly therefrom, an RFID tag including predetermined tracking capabilities disposed on said flag structure, a tamper evident structure disposed on said housing in removable restricting relation to said tip cap, from said hollow interior via said access opening and said tamper evident structure comprising an aperture disposed in communicating alignment with said access opening concurrent to said removal restricting relation to said tip cap; said aperture having a diametrical dimension less than a corresponding diametrical dimension of said access opening.

2. The closure assembly as recited in claim 1 wherein the said RFID tag is removably disposed on said flag structure.

3. The closure assembly as recited in claim 2 wherein said RFID tag is structured for attachment to the medical container subsequent to removal from said flag structure.

4. The closure assembly as recited in claim 1 wherein said tamper evident structure is integrated in said flag structure and concurrently connected to said housing with said tamper evident structure.

5. The closure assembly as recited in claim 1 wherein said tamper evident structure is disposed on said housing and dimensioned and configured to extend inwardly from a periphery of said access opening, towards a center thereof and into overlying relation to said hollow interior, concurrent to disposition of said tamper evident structure in said removable restricting relation to said tip cap.

6. The closure assembly as recited in claim 1 wherein a diametrical dimension of said tip cap is less than said diametrical dimension of said access opening and greater than said diametrical dimension of said aperture; a diametrical dimension of a connecting portion of the medical container being less than said diametrical dimension of said aperture.

7. The closure assembly as recited in claim 6 wherein said diametrical dimensions of said tip cap, said access opening and said aperture define an unrestricted passage of said tip cap through said access opening concurrent to a rupturing of said tamper evident structure, upon passage of said tip cap through said aperture.

8. The closure assembly as recited in claim 7 wherein said tamper evident structure is at least partially formed of a material capable of being torn.

9. The closure assembly as recited in claim 1 wherein said flag structure comprises a base, said tamper evident structure connected to said base and including a substantially annular configuration disposed in substantially surrounding relation to said aperture.

10. The closure assembly as recited in claim 9 wherein said base and said tamper evident structure are disposed in overlying at least partially covering relation to said access opening, said tamper evident structure concurrently disposed in interruptive engaging relation to said tip cap, upon passage of said tip cap through said access opening.

11. The closure assembly as recited in claim 10 wherein said tamper evident structure is formed of a foil material disposed contiguous to an inner periphery of said aperture.

12. The closure assembly as recited in claim 1 wherein said tamper evident structure is mounted on said housing in covering relation to said access opening and in enclosing relation to said hollow interior, said tamper evident structure including a secondary RFID tag mounted thereon in spaced relation to said RFID tag disposed on said flag structure.

13. The closure assembly as recited in claim 12 wherein said tamper evident structure is formed of a material, penetrable by passage of the medical container therethrough into accessible relation with said tip cap, via said access opening; said secondary RFID tag, including predetermined tracking capabilities and being disposed and structured for deactivation substantially concurrent to penetration of said tamper evident structure by the medical container.

14. A closure assembly for a medical container comprising:

a plurality of closures each including a housing having a hollow interior and an access opening communicating with said hollow interior, a tip cap removably disposed within said hollow interior of each of said plurality of closures, in an accessible disposition by the medical container, via said access opening, a plurality of flag structures each connected to a different one of said housings and extending outwardly therefrom, each of said plurality of closures including a tamper evident structure disposed on said housing in removable restricting relation to said tip cap, from said hollow interior, via said access opening and said tamper evident structure comprising an aperture disposed in communicating alignment with said access opening concurrent to said removal restricting relation to said tip cap; said aperture having a diametrical dimension less than a corresponding diametrical dimension of said access opening.

15. The closure assembly as recited in claim 14 comprising said plurality of closures disposed in a capping orientation, said capping orientation facilitating volume capping of said tip caps with the medical containers.

16. The closure assembly as recited in claim 15 wherein said capping orientation comprises an aligned strip of said plurality of closures disposed in interconnected relation to one another.

17. The closure assembly as recited in claim 16 wherein said interconnected relation of said plurality of closures comprises removable attachment of said flag structures of adjacent ones of said plurality of closures along a length of said strip.

18. The closure assembly as recited in claim 17 wherein each of said flag structures comprises a base connected to said housing and an arm connected to said base and extending outwardly from said base and a respective one of said plurality of closures, into said removable attachment with said arms of adjacent ones of said flag structures.

19. The closure assembly as recited in claim 14 further comprising an RFID tag including predetermined tracking capabilities disposed on said flag structure.

* * * * *